US009284532B2

(12) United States Patent
Guelen et al.

(10) Patent No.: US 9,284,532 B2
(45) Date of Patent: Mar. 15, 2016

(54) MAMMALIAN CELLS FOR PROPAGATING VIRUS

(71) Applicant: Intervet Inc., Summit, NJ (US)

(72) Inventors: Lars Guelen, Nijmegen (NL); Carla Christina Schrier, Boxmeer (NL)

(73) Assignee: Intervet Inc., Madison, NJ (US)

( * ) Notice: Subject to any disclaimer, the term of this patent is extended or adjusted under 35 U.S.C. 154(b) by 21 days.

(21) Appl. No.: 14/108,685

(22) Filed: Dec. 17, 2013

(65) Prior Publication Data

US 2014/0178967 A1 Jun. 26, 2014

(30) Foreign Application Priority Data

Dec. 21, 2012 (EP) .................................... 12199169

(51) Int. Cl.
*C12N 7/00* (2006.01)
*C12N 15/113* (2010.01)

(52) U.S. Cl.
CPC .............. *C12N 7/00* (2013.01); *C12N 15/1136* (2013.01); *C12N 2510/02* (2013.01); *C12N 2770/10051* (2013.01)

(58) Field of Classification Search
None
See application file for complete search history.

(56) References Cited

U.S. PATENT DOCUMENTS

| | | | | |
|---|---|---|---|---|
| 2006/0051369 | A1* | 3/2006 | Taylor et al. | 424/199.1 |
| 2014/0178967 | A1* | 6/2014 | Guelen et al. | 435/235.1 |

FOREIGN PATENT DOCUMENTS

WO 2010/123501 A1 10/2010

OTHER PUBLICATIONS

Overend et al. (Journal of General Virology. 2007; 88; 925-931).*
Mosca et al. (Molecular and Cellular Biology. 1986; 6 (6): 2279-2283).*
Zhang et al. (International Journal of Cancer; 2010; 127: 830-838).*
Luo et al. (Molecular Immunology. 2008; 45: 2839-2846).*
He et al. (Veterinary Immunobiology and Immunopathology. 2011; 139: 57-60).*
Miller et al. (Archives of Virology. 2004; 149: 2453-2463).*
Song, S. et al., Porcine reproductive and respiratory syndrome virus infection activates IL-10 production through NF-[kappa]B and p38 MAPK pathways in porcine alveolar macrophages, Developmental & comparative immunology, Oct. 22, 2012, pp. 265-272, vol. 39, No. 3, WO.
Calvert, et al., “CD163 Expression Confers Susceptibility to Porcine Reproductive and Respiratory Syndrome Viruses”, Journal of Virology, 2007, p. 7371-7379, vol. 81(14).
Kim, et al., “Defining the Cellular Target(s) of Porcine Reproductive and Respiratory Syndrome Virus Blocking Monoclonal Antibody 7G10”, Journal of Virology, 2006, pp. 689-696, vol. 80(2).
St-Louis, et al., “The Equine Arteritis Virus Induces Apoptosis Via Caspase-8 and Mitochondria-Dependent Caspase-9 Activation”, Virology, 2007, pp. 147-155, vol. 367.
Wieringa, et al., “Structural Protein Requirements in Equine Arteritis Virus Assembly”, Journal of Virology, 2004, pp. 13019-13027, vol. 78(23).
Zheng, et al., “Baculovirus Expression of Cloned Porcine Arterivirus Generates Infectious Particles in Both Insect and Mammalian Cells”, Journal of Biotechnology, 2010, pp. 251-258, vol. 150.
Beura, et al., “Cellular Poly(C) Binding Proteins 1 and 2 Interact with Porcine Reproductive and Respiratory Syndrome Virus Nonstructural Protein 1β and Support Viral Replication”, Journal of Virology, 2011, pp. 12939-12949, vol. 85(24).
Wang, et al., Molecular cloning and functional characterization of porcine IFN-β promoter stimulator 1 (IPS-1), Veterinary Immunology and Immunopathology, 2008, pp. 344-353, vol. 125.
Wang, et al., “MiR-125b Reduces Porcine Reproductive and Respiratory Syndrome Virus Replication by Negatively Regulating the NF-kB Pathway”, PLOS One, 2013, pp. 1-12 (e55838), vol. 8(2).
Welch, et al., “A brief review of CD163 and its role in PRRSV infection”, Virus Research, 2010, pp. 98-103, vol. 154.
European Search Report for corresponding EP Application No. EP 12 19 9169, dated Jun. 3, 2013.

* cited by examiner

*Primary Examiner* — Shanon A Foley

(57) ABSTRACT

The present invention relates to mammalian cells capable of propagating Arterivirus, to such cells infected with Arterivirus, to cell cultures comprising such cells and to methods for the propagation of an Arterivirus in such cells.

17 Claims, 6 Drawing Sheets

Figure 2:
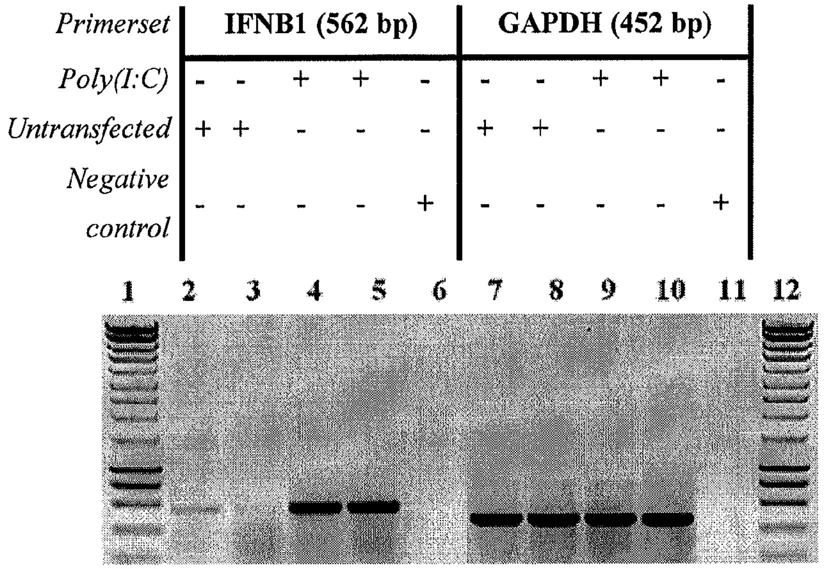

```
                      10        20        30        40        50        60        70        80
                       *         *         *         *         *         *         *         *
NM_002176      acattctaactgcaacctttcgaagcctttgctctggcacaacaggtagtaggcgacactgttcgtgttgtcaacatgac
NM_001135795   ---------------------------------------------------------------------------atgac

                      90       100       110       120       130       140       150       160
                       *         *         *         *         *         *         *         *
NM_002176      caacaagtgtctcctccaaattgctctcctgttgtgcttctccactacagctctttccatgagctacaacttgcttggat
NM_001135795   caacaagtgtctcctccaaattgctctcctgttgtgcttctccactacggctctttccatgagctacaacttgcttggat

                     170       180       190       200       210       220       230       240
                       *         *         *         *         *         *         *         *
NM_002176      tcctacaaagaagcagcaattttcagtgtcagaagctcctgtggcaattgaatgggaggcttgaatactgcctcaaggac
NM_001135795   tcctacaaagaagcagcagttttcagtgtcagaagctcctgtggcaattgaatggaaggcttgaatactgcctcaaggac

                     250       260       270       280       290       300       310       320
                       *         *         *         *         *         *         *         *
NM_002176      aggatgaactttgacatccctgaggagattaagcagctgcagcagttccagaaggaggacgccgcattgaccatctatga
NM_001135795   aggatgaactttgacatccctgaggaaattaagcagccgcagcagttccagaaggaggacgctgcattgaccatctatga

                     330       340       350       360       370       380       390       400
                       *         *         *         *         *         *         *         *
NM_002176      gatgctccagaacatctttgctattttcagacaagattcatctagcactggctggaatgagactattgttgagaacctcc
NM_001135795   gatgctccagaacatcttcgctattttcagacaagatttatctagcactggctggaatgagactattgtggagaacttcc

                     410       420       430       440       450       460       470       480
                       *         *         *         *         *         *         *         *
NM_002176      tggctaatgtctatcatcagataaaccatctgaagacagtcctggaagaaaaactggagaaagaagatttcaccagggga
NM_001135795   ttgctaatgtctatcatcagatagaccatctgaagacaatcctagaagaaaaactggagaaagaagatttcaccagggga

                     490       500       510       520       530       540       550       560
                       *         *         *         *         *         *         *         *
NM_002176      aaactcatgagcagtctgcacctgaaaagatattatgggaggattctgcattacctgaaggccaaggagtacagtcactg
NM_001135795   aaattcatgagcagtttgcacctgaaaagatactatggaaggattctgcattacctgaaggccaaggagtacagtcactg

                     570       580       590       600       610       620       630       640
                       *         *         *         *         *         *         *         *
NM_002176      tgcctggaccatagtcagagtggaaatcctaaggaacttttacttcattaacagacttacaggttacctccgaaactgaa
NM_001135795   tgcctggaccatagtcagagtggaaatcctcaggaacttttttcttcattaacaaacttacaggttacctccgaaactga-

                     650       660       670       680       690       700       710       720
                       *         *         *         *         *         *         *         *
NM_002176      gatctcctagcctgtgcctctgggactggacaattgcttcaagcattcttcaaccagcagatgctgtttaagtgactgat
NM_001135795   --------------------------------------------------------------------------------

                     730       740       750       760       770       780       790       800
                       *         *         *         *         *         *         *         *
NM_002176      ggctaatgtactgcatatgaaaggacactagaagattttgaaattttattaaattatgagttatttttatttatttaaa
NM_001135795   --------------------------------------------------------------------------------

                     810       820       830       840
                       *         *         *         *
NM_002176      ttttattttggaaaataaattatttttggtgcaaaagtca
NM_001135795   ----------------------------------------
```

Figure 1: Alignment interferon beta sequences

A
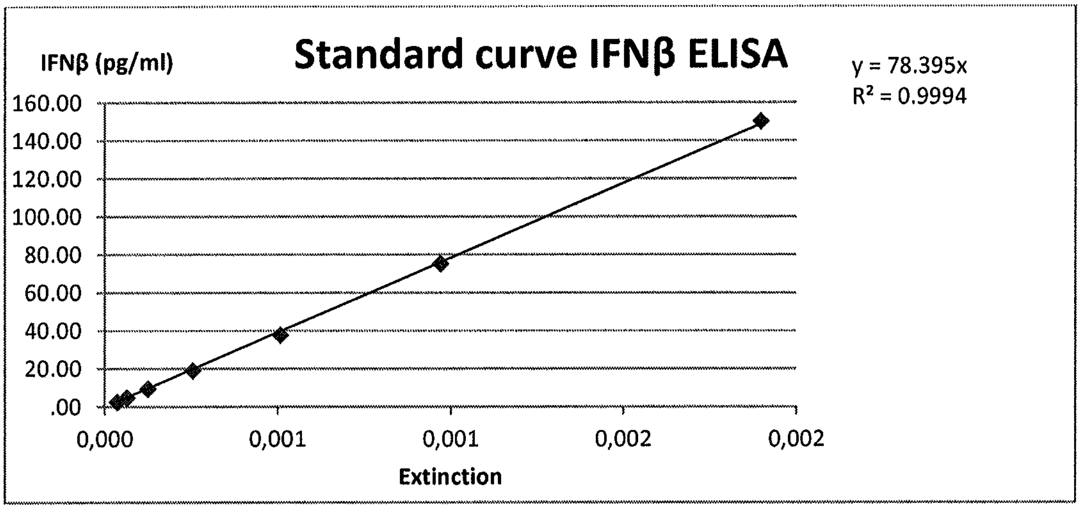
B
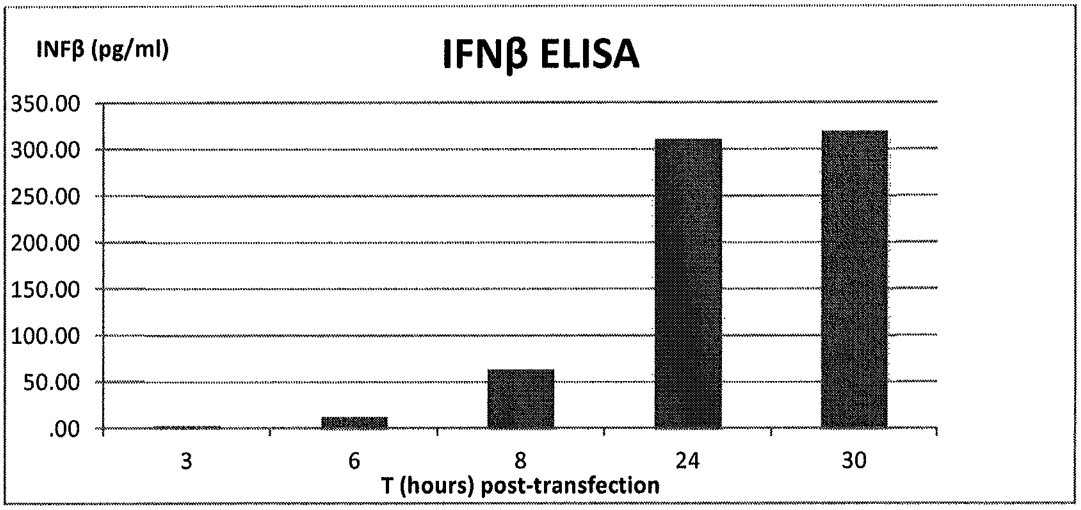
Figure 4.

A
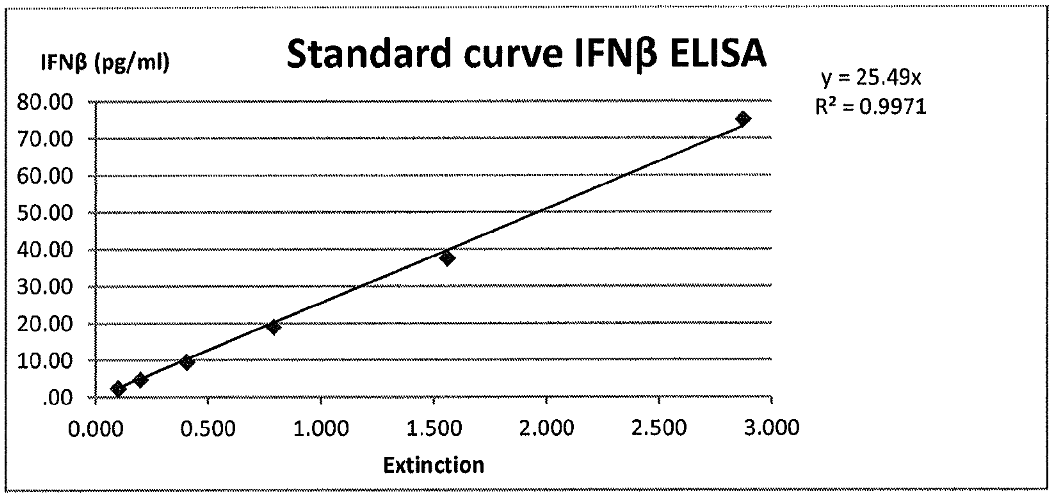
B
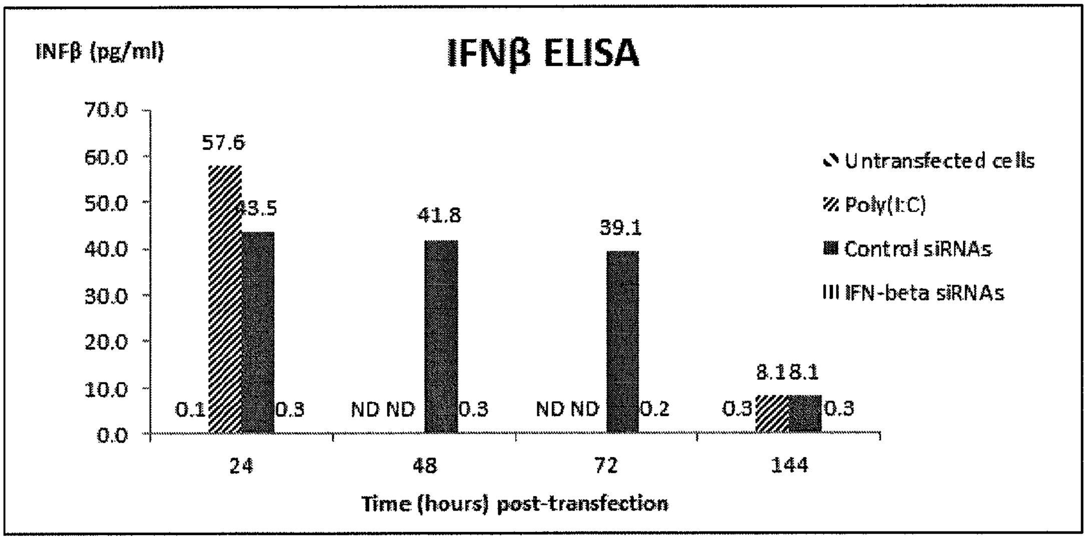
Figure 6.

SEQUENCE LISTING

```
<160> NUMBER OF SEQ ID NOS: 12

<210> SEQ ID NO 1
<211> LENGTH: 21
<212> TYPE: DNA
<213> ORGANISM: Homo sapiens

<400> SEQUENCE: 1

atgaccaaca agtgtctcct c                                               21


<210> SEQ ID NO 2
<211> LENGTH: 22
<212> TYPE: DNA
<213> ORGANISM: Homo sapiens

<400> SEQUENCE: 2

agtttcggag gtaacctgta ag                                              22


<210> SEQ ID NO 3
<211> LENGTH: 20
<212> TYPE: DNA
<213> ORGANISM: Homo sapiens

<400> SEQUENCE: 3

accacagtcc atgccatcac                                                 20
```

-continued

<210> SEQ ID NO 4
<211> LENGTH: 20
<212> TYPE: DNA
<213> ORGANISM: Homo sapiens

<400> SEQUENCE: 4
tccaccaccc tgttgctgta 20

<210> SEQ ID NO 5
<211> LENGTH: 25
<212> TYPE: RNA
<213> ORGANISM: Homo sapiens

<400> SEQUENCE: 5
ccuguggcaa uugaauggaa gucuu 25

<210> SEQ ID NO 6
<211> LENGTH: 25
<212> TYPE: RNA
<213> ORGANISM: Homo sapiens

<400> SEQUENCE: 6
aagacuucca uucaauugcc acagg 25

<210> SEQ ID NO 7
<211> LENGTH: 25
<212> TYPE: RNA
<213> ORGANISM: Homo sapiens

<400> SEQUENCE: 7
uagcacuggc uggaaugaga cuauu 25

<210> SEQ ID NO 8
<211> LENGTH: 25
<212> TYPE: RNA
<213> ORGANISM: Homo sapiens

<400> SEQUENCE: 8
aauagucuca uuccagccag ugcua 25

<210> SEQ ID NO 9
<211> LENGTH: 25
<212> TYPE: RNA
<213> ORGANISM: Homo sapiens

<400> SEQUENCE: 9
aauucaugag cagucugcac cugaa 25

<210> SEQ ID NO 10
<211> LENGTH: 25
<212> TYPE: RNA
<213> ORGANISM: Homo sapiens

<400> SEQUENCE: 10
uucaggugca gacugcucau gaauu 25

<210> SEQ ID NO 11
<211> LENGTH: 840
<212> TYPE: DNA
<213> ORGANISM: Homo sapiens

<400> SEQUENCE: 11

-continued

```
acattctaac tgcaaccttt cgaagccttt gctctggcac aacaggtagt aggcgacact     60

gttcgtgttg tcaacatgac caacaagtgt ctcctccaaa ttgctctcct gttgtgcttc    120

tccactacag ctctttccat gagctacaac ttgcttggat tcctacaaag aagcagcaat    180

tttcagtgtc agaagctcct gtggcaattg aatgggaggc ttgaatactg cctcaaggac    240

aggatgaact ttgacatccc tgaggagatt aagcagctgc agcagttcca gaaggaggac    300

gccgcattga ccatctatga gatgctccag aacatctttg ctattttcag acaagattca    360

tctagcactg gctggaatga gactattgtt gagaacctcc tggctaatgt ctatcatcag    420

ataaaccatc tgaagacagt cctggaagaa aaactggaga aagaagattt caccagggga    480

aaactcatga gcagtctgca cctgaaaaga tattatggga ggattctgca ttacctgaag    540

gccaaggagt acagtcactg tgcctggacc atagtcagag tggaaatcct aaggaacttt    600

tacttcatta acagacttac aggttacctc cgaaactgaa gatctcctag cctgtgcctc    660

tgggactgga caattgcttc aagcattctt caaccagcag atgctgttta agtgactgat    720

ggctaatgta ctgcatatga aaggacacta gaagattttg aaatttttat taaattatga    780

gttattttta tttatttaaa ttttattttg gaaaataaat tatttttggt gcaaaagtca    840


<210> SEQ ID NO 12
<211> LENGTH: 564
<212> TYPE: DNA
<213> ORGANISM: Macaca mulatta

<400> SEQUENCE: 12

atgaccaaca agtgtctcct ccaaattgct ctcctgttgt gcttctccac tacggctctt     60

tccatgagct acaacttgct tggattccta caaagaagca gcagttttca gtgtcagaag    120

ctcctgtggc aattgaatgg aaggcttgaa tactgcctca aggacaggat gaactttgac    180

atccctgagg aaattaagca gccgcagcag ttccagaagg aggacgctgc attgaccatc    240

tatgagatgc tccagaacat cttcgctatt ttcagacaag atttatctag cactggctgg    300

aatgagacta ttgtggagaa cttccttgct aatgtctatc atcagataga ccatctgaag    360

acaatcctag aagaaaaact ggagaaagaa gatttcacca ggggaaaatt catgagcagt    420

ttgcacctga aaagatacta tggaaggatt ctgcattacc tgaaggccaa ggagtacagt    480

cactgtgcct ggaccatagt cagagtggaa atcctcagga actttttctt cattaacaaa    540

cttacaggtt acctccgaaa ctga                                           564
```

MAMMALIAN CELLS FOR PROPAGATING VIRUS

The present invention relates to mammalian cells capable of propagating Arterivirus, to such cells infected with Arterivirus, to cell cultures comprising such cells and to methods for the propagation of an Arterivirus in such cells.

The Arterivirus family comprises the Equine arteritis virus (EAV), Porcine respiratory and reproductive syndrome virus (PRRSV), Lactate dehydrogenase elevating virus (LDV), and Simian hemorrhagic fever virus (SHFV). Of these four virus species, LDV and SHFV have only minor economic impact, since they infect mice and monkeys respectively. Contrary to this, EAV and especially PRRSV pose a considerable financial burden on society.

Equine arteritis virus causes infections in horses, and thus forms a recurring problem in the horse breeding industry. Therefore it poses a significant economic burden on horse breeders. The Equine arteritis virus establishes a persistent infection in so-called "carrier stallions", which subsequently transmit the virus to mares, potentially leading to abortion of foetuses. Horse breeders carefully monitor the presence of EAV, especially in stallions, and a number of vaccines have been developed against the virus based on live attenuated virus or based on expression of EAV structural subunits. However, recent outbreaks in New Mexico, US (2006) and France (2007) have further increased interest in EAV and EAV-vaccines among veterinarians and horse owners.

PRRSV is by far the most economically important Arterivirus, affecting swine farming industries around the world. Infection with this virus results in slow growth, decreased feed efficiency, anorexia, and fever in weaning to finishing pigs, abortion in pregnant sows and respiratory problems in young pigs. In the US alone, yearly losses associated with PRRSV infection were estimated to lie around $560 million in 2005 and $664 million in 2011. PRRSV infection ranks as the number one health challenge for the pig industry, causing the greatest productivity losses when compared to other diseases caused by for example *Clostridium difficile*, swine influenza, *Streptococcus* sp., rotavirus or porcine circovirus. Considering the emergence of highly virulent strains of PRRSV in South-East Asia in 2006 and the fact that the Asian swine industry is the largest in the world, it can safely be assumed that losses in this part of the world are considerably higher than those reported for the US. PRRSV remains a major threat to the swine industry since the associated disease has proven to be difficult to control, in spite of the availability of both live attenuated and killed vaccines against PRRSV.

The Arterivirus family consists of positive-sense (+) single-stranded RNA viruses with a genome size ranging from about 13 to 16 kb. Upon infection, the RNA is translated into two replicase precursor polyproteins, pp1a and pp1ab. The functional non-structural proteins (nsps) of Arteriviruses derive from cleavage of these polyproteins by their internal protease activity. Upon release from the polyprotein, these non-structural proteins together form the replication and transcription complex which is responsible for the replication of the viral genome and for the synthesis of the subgenomic messenger RNAs encoding the structural proteins. The pp1a and pp1ab polyproteins of the prototype Arterivirus, EAV, are cleaved into at least 13 nonstructural proteins by three internal proteases present in nonstructural protein 1 (nsp1), nsp2 and nsp4.

Arteriviral nsp2 contains a papain-like protease (PLP) domain in its N-terminal region. PLP2, as this protease is commonly referred to, is responsible for the cleavage of the junction between nsp2 and nsp3, and its catalytic activity is, likely for this reason, essential for viral replication.

For most virus species it goes that, upon infection, the presence of viral nucleic acids triggers the activation of innate immune signaling cascades, resulting in the activation of transcription factors such as NF-κβ and Irf3/Irf7, ultimately leading to the transcription of genes encoding beta interferon (IFN-β) and other pro-inflammatory cytokines.

This so-called innate immunity provides a very useful natural defense of the host against viruses. However, this same innate immunity forms a problem for vaccine producers. Whole virus vaccines are normally produced by propagating (wild-type or attenuated) virus in vitro, e.g. in cell culture, followed by harvesting of the progeny virus. As a result of the innate immunity, the amount of virus produced in vitro is often quite low: the induction of INF-β leads to protection of other cells against the invasion (and subsequent replication) of the virus.

For several virus species, this problem can theoretically be tackled by decreasing the amount of IFN-β produced.

However, in the case of Arteriviruses this approach is considered to have no effect for the following reason: Arteriviruses are known to very efficiently evade the host's innate immune responses. These strong immune-modulatory capabilities of Arteriviruses prevent the induction of an efficient immune response against wild type PRRSV and against live attenuated PRRSV. Therefore the level of immunity that can be induced is suboptimal for protecting against field infections.

The cause of this immune evasive character of Arteriviruses is known. It is caused by the nsp2 protein of Arteriviruses which in addition to its role in polyprotein processing plays a very strong role in the evasion of host innate immune responses.

Comparative sequence analysis showed that the PLP2 domain of this protein displays a similarity to proteins belonging to the ovarian tumor domain-containing (OTU) class of de-ubiquitinating enzymes (DUBs) (Makarova (2000)). It has since then been confirmed that Arteriviral PLP2 indeed possess genuine DUB activity and that this activity is likely employed to remove ubiquitin (further also referred to as Ub) from innate immune signaling factors to suppress the induction of an antiviral state (Frias-Staheli, N. (2007), Sun, Z. (2010), van Kasteren, P. B. (2012)). In addition to its DUB activity, arteriviral PLP2 has also been shown to remove the ubiquitin-like antiviral protein Interferon Stimulated Gene 15 (ISG15) from cellular target proteins (Frias-Staheli, N. (2007), Sun, Z. (2012), Arguello, M. D. (2007)). This activity will be referred to as the deISGylating activity. Due to the close relatedness of ubiquitin and ISG15, this role of the PLP2 domain will generally be referred to as the DUB/deISGylating activity.

It is this DUB/deISGylating activity that, through suppression of the induction of an antiviral state, allows the virus to circumvent the host's first defense.

This characteristic of Arteriviruses to evade the cell's innate immune system through a blockade of INF-β induction understandably has an in vitro consequence: propagation in vitro in susceptible cells such as the commercially available MA104 cells and Marc145 cells often used for propagating PRRSV, is not expected to be influenced by the innate immune system: the virus itself already blocks the induction of IFN-β.

Therefore, in the case of Arteriviruses, measures to decrease the amount of IFN-β produced by such cells with the aim of producing more viruses in vitro were not expected to have any effect on the virus titer. As said above, Arteriviruses by nature block the production of IFN-β in the host cell in vitro, analogous to the situation in in vivo growth in a host.

It was now surprisingly found, however, that a deliberate blocking of IFN-β production in cells, additional to the blocking effect of the Arterivirus itself, resulted in a very significant increase of the amount of progeny Arterivirus propagated in these cells. Even an increase in virus titer of up to a factor 6-7 is frequently obtained. For reasons explained above, this is indeed unexpected given the known Arteriviral blocking of IFN-β production.

Thus, a first embodiment of the present invention relates to a mammalian cell capable of propagating an Arterivirus, characterised in that said cell is deficient in its IFN-β production.

Propagation of a virus in a cell is the process that comprises the replication of a virus in that cell, as a result of which progeny virus emerges. A mammalian cell capable of propagating an Arterivirus thus is a cell capable of producing progeny virus of said Arterivirus.

For the purpose of this invention, a mammalian cell according to the invention that is deficient in its IFN-β production is a mammalian cell that after stimulation of the IFN-β pathway shows an increase in IFN-β to a level that is half or less than half the amount of IFN-β produced by a wild-type form of that mammalian cell under the same stimulation conditions. Preferably, a mammalian cell according to the invention shows an increase in IFN-β that is below 40%, more preferably below 30%, below 20%, below 10% or even below 5%, in that order of preference, of the amount of IFN-β shown by a wild-type form of that mammalian cell under the same stimulation conditions. The level of IFN-β can be determined by means of an ELISA.

In the Examples section, a description is given of an ELISA reaction that can be used to determine the level of increase of IFN-β protein after stimulation of the IFN-β pathway. In the Examples, a method is provided to determine and compare the level of IFN-β in wild-type cells and cells according to the invention.

The test as described uses commercially available antibodies for the determination of the amount of IFN-β produced by cells. It goes without saying that a test using another antibody reactive with IFN-β can equally be used.

In a preferred mammalian cell according to the invention, the unexpected effect is achieved by blocking the translation of IFN-β mRNA into IFN-β protein by introducing anti-IFN-β siRNAs into the host cell.

This approach is based upon the gene-silencing effect of double-stranded siRNAs (short interfering/inhibitory RNAs in any form, e.g. in the form of short hairpins) on gene expression. The principle and mechanism behind this so-called RNA interference, shortly referred to as RNAi, and behind siRNA have been the subject of many publications over the last decade. The main use of RNAi still is, and has been, the specific silencing of genes of the host or host's cells under study in order to determine their role in the host. Reviews on this topic have been written by Hannon, G. J. in Nature 418: 244-251 (2002) and by Deni, A. M. and Hannon, G. J. in TRENDS in Biochemical Sciences 28: 196-201 (2003). Other papers, describing the use of siRNA in gene silencing are by Bertrand, J. R. et al., in B.B.R.C. 296: 1000-1004 (2002) and by Sorensen, D. R. et al., in J. Mol. Biol. 327: 761-766 (2003). An extensive review on siRNA was published by Dorsett, Y. and Tuschl, T. in Nature Reviews, Drug Discovery 3: 318-329 (2004).

In order to obtain an optimal base pair matching between the siRNA and the IFN-β mRNA from the target cells, in this case Marc145 cells, the inventors have first made an alignment of the sequences of two primate IFN-β genes currently available in gene banks. As a next step, (RT)-PCR-primers were developed on the basis of highly conserved regions in these primate IFN-β genes. These PCR-primers were used to produce IFN-β DNA of IFN-β mRNA from Marc145 cells. The Marc145-specific IFN-β DNA so obtained was sequenced and the sequence information was used to develop the siRNAs used for gene silencing. By following this approach, it could be ascertained that the siRNAs show optimal binding to the target IFN-β mRNA. (See the Examples section for details).

For the gene silencing experiment, mammalian cells capable of propagating Arterivirus, in this case Marc145 cells, were cultured and transfected with the anti-Marc145 IFN-β siRNA with Poly(I:C) RNA being added as IFN-β stimulator. About 5-6 hours after transfection with siRNA's, the cells were infected with PRRSV. (See the Examples section for details). As can be seen from FIG. 7, an increase in titre of about 6-7 times could easily be obtained.

The transfection process described is very suitable to achieve the unexpected effect of decreasing the amount of IFN-β in small scale in vitro culture. However, as a process for decreasing the amount of IFN-β in large scale in vitro culture for large scale virus production, it is not particularly suitable.

In order to obtain a decrease of the amount of IFN-β in cells in in vitro culture for large scale virus production, the skilled person can however choose one of many options, all known in the art.

One option is the introduction into the cell of a plasmid carrying a short DNA fragment encoding anti-IFN-β siRNA under the control of a mammalian promoter. This avoids the necessity of transfecting cells each time an in vitro culture of virus is started.

Such a plasmid can be a plasmid that remains present in the cytoplasm of the cell and constitutively produces a certain amount of siRNA. Preferably, the plasmid integrates in the cellular genome. Such plasmids are well-known in the art. Cells carrying such a plasmid are deficient in their IFN-β production but they do not require culturing under selective pressure, as would be the case if the plasmid was not integrated in the genome.

It is equally possible to obtain cells according to the invention that are deficient in their IFN-β production, by developing an siRNA capable of silencing one of the other genes that are involved in the IFN-β pathway.

The interferon pathway is known to be a cascade of events that is triggered by the entry of (in this case) a single-stranded RNA virus into the cell. The virus enters an endosome of the cell through endocytosis, where it triggers the Toll-like Receptor TLR7. Activated TLR7 recruits the adaptor MyD88 that in turn recruits IRAK-4 and IRAK-1. This complex acts as a scaffold to components that trigger the NF-κB and Irf3/Irf7 pathway. This ultimately leads to the transcription of genes encoding IFN-β and other pro-inflammatory cytokines.

The whole cascade is well-known for many years already, and the proteins involved are known. Extensive reviews of the IFN-β pathway are e.g. written by Taro Kawai and Shizuo Akira in Nature Immunology 7: 131-137 (2006), by Akinori Takaoka and Hideyuki Yanai in Cellular Microbiology 8: 907-922 (2006), by Osamu Takeuchi and Shizuo Akira in Immunological Reviews 220: 214-224 (2007), and most extensively by Randall, R. E. and Goodbourn, S., in Journal of General Virology 89: 11-47 (2008).

Once an amount of IFN-β is formed, it is excreted by the cell. The excreted IFN-β subsequently binds to the IFN-α/β receptor that protrudes from the cell membrane This binding induces a further increase in the production of IFN-β and also induces IFN-α, in both the cells that originally produced the IFN-β (e.g. as a result of the virus infection) and in the surrounding cells.

For this reason, the IFN-α/β receptor is considered to be a part of the interferon-β pathway. A further task of the IFN-α/β receptor is the induction of the so-called JAK/STAT pathway that finally interferes with the formation of progeny virus.

Since the IFN-α/β receptor is part of the interferon-β pathway, the IFN-α/β receptor is an equally suitable target for siRNA targeting. Down-regulation of the receptor is described i.a. by Kai-xin Zhang et al., in International Journal of Cancer 127: 830-838 (2010). Background information of the IFN-α/β receptor can i.a. be found in review papers by Platanias, L. C. (Nature Reviews Immunology 5: 375-386 (2005), by Randall, R. E. and Goodbourn, S. (vide supra) and by Akinori Takaoka and Hideyuki Yanai (vide supra).

Thus, a preferred form of this embodiment relates to a mammalian cell according to the invention, characterised in that said cell comprises a DNA fragment encoding an siRNA under the control of a suitable promoter, that is capable of silencing one of the genes of the IFN-β pathway.

An equally attractive way to obtain a mammalian cell according to the invention that is deficient in their IFN-β production is to introduce a mutation in a gene that is involved in the IFN-β pathway. Such a mutation can be an insertion, a deletion or replacement mutation, provided of course that the mutation leads to a cell according to the invention that is deficient in its IFN-β production, as defined above. The most efficient way is to not just make a mutation in such a gene, but to simply delete one of the genes involved in the IFN-β pathway.

If genes mentioned above are selected to be silenced and/or mutated, care should be taken to avoid that an alternative sub-route of the cascade takes over the blocked sub-route. Merely as an example; if IRF7 would be mutated, preferably NF-κB should be mutated as well. (For a full overview of the pathways, see i.a. Randall, R. E. and Goodbourn, S., in Journal of General Virology 89: 11-47 (2008) as mentioned above).

Of course, a very attractive and thus preferred gene to mutate is the gene encoding IFN-β itself. This can be done i.a. by mutating the gene as such, but it can also be accomplished by e.g. mutating the IFN-β promoter or elements of the promoter region such as PRD IV, PRD I/III or PRD II.

Thus, an equally preferred form of this embodiment relates to a mammalian cell according to the invention, characterised in that said cell has a mutation in a gene of the IFN-β pathway.

Genes of the IFN-β pathway that are suitable as gene silencing targets and as mutation targets are i.a. the genes encoding IFN-β, the IFN-α/β receptor, MyD88, IRAK-4, IRAK-1, TRAF3, TRAF6, TAK1, TAB2, TAB3, RIP1, the genes encoding the proteins of the IKK-complex, more specifically the IKK-β subunit and the IKK-α subunit, and the genes encoding NF-κB and IRF7.

Thus, a more preferred form of either preferred form of the present invention relates to a mammalian cell according to the invention, characterised in that said gene is selected from the group of genes consisting of the genes encoding IFN-β, the IFN-α/β receptor, MyD88, IRAK-4, IRAK-1, TRAF3, TRAF6, TAK1, TAB2, TAB3, RIP1, the genes encoding the IKK-β subunit and the IKK-α subunit proteins of the IKK-complex, and the genes encoding NF-κB and IRF7.

The skilled person desiring to mutate any of the genes mentioned above has several powerful tools for specific gene mutation available such as e.g. zink finger nucleases (ZNF's) and Transcription Activator Like Effector Nucleases (TALEN's).

These tools are the tools of choice for the specific mutation of any gene. Basically, both tools rely on the fact that they comprise a dimerised DNAse FokI, capable of creating double-stranded breaks anywhere in DNA, and two highly specific and investigator-designed DNA binding domains. Both TALEN's and ZFN's allow highly specific gene targeting and gene mutation.

These tools and their uses have extensively been described for the mutation of genes in i.a. cells, pluripotent cells and embryos. A few examples of publications are given here: DeFrancesco, L. in Nature Biotechnology 29, 681-684 (2011), Cost, G. et al., in Nature Biotechnology 29, 695-696 (2011), Yeh, J-R. et al., in Nature Biotechnology 29, 697-698 (2011), Zhang, B. et al., Nature Biotechnology 29, 699-700 (2011), Jaenisch, R. et al., in Nature Biotechnology 29, 731-734 (2011), Miller, J. et al., in Nature Biotechnology 29, 143-148 (2011) and Zhang, F. et al., in Nature Biotechnology 29, 149-153 (2011). A ZFN-review by Hauschild-Quintern, J et al., is available in electronic form from Cellular and Molecular Life Sciences, Springer Basel 2012 10.1007/s00018-012-1204-1.

Cells in which one or more specific genes are mutated by using one of these two techniques are currently also commercially available on demand.

Thus, the skilled artisan wanting to avoid the effort of mutating a gene from the INF-β pathway, can e.g. order cells in which the desired gene has been mutated using TALEN's on demand from Cellectis bioresearch, 8 rue de la Croix Jarry, 75013 Paris, France or from Cellectis bioresearch Inc., One Broadway, Cambridge, Mass. 02142, USA.

Cells in which the desired gene has e.g. been mutated using ZFN's are commercially available on demand from From Sigma-Aldrich Corporation, 3050 Spruce Street, St. Louis, Mo. 63103 USA.

The approaches described above are all equally applicable to increase the yield of Equine Arteritisvirus (EAV) in cell culture. This virus is usually grown on Baby Hamster Kidney BHK21 cells and Rabbit Kidney RK13 cells. The sequence of the IFN-β mRNA of RK13 cells is given by the NCBI under number XM_002707968.1. Therefore, e.g. an siRNA for gene silencing in RK13 cells can directly be designed on the basis of this sequence. Equally, highly specific and investigator-designed DNA binding domains for use in TALEN's or ZFN's can directly be designed on the basis of this sequence.

Thus, in an even more preferred form of this embodiment the mammalian cell according to the invention is a mammalian cell that is capable of propagating PRRSV or EAV.

In a still even more preferred form of this embodiment, the mammalian cell according to the invention is selected from the group of mammalian cells that consist of BHK21, RK13, MA104 or Marc145.

Another embodiment of the present invention relates to methods for the propagation of an Arterivirus in cell culture, wherein said methods comprise the step of propagating said Arterivirus on mammalian cells according to the invention.

Again another embodiment of the present invention relates to a mammalian cell according to the invention, characterised in that said mammalian cell is infected with an Arterivirus.

Still another embodiment of the present invention relates to a cell culture comprising mammalian cells according to the invention.

A preferred form of that embodiment relates to a cell culture comprising mammalian cells according to the invention, characterised in that said mammalian cells are infected with an Arterivirus.

LEGEND TO THE FIGURES

FIG. 1: Alignment of *Macaca mulatta* (SEQ ID NO: 2) and *Homo sapiens* (SEQ ID NO: 1) Interferon-β sequences.

FIG. 2: IFN-β expression after transfection with poly(I:C) at T=24 hours post transfection. Lanes 2, 3, 7 and 8 show untransfected cells, lanes 4, 5, 9 and 10 show the effect if poly(I:C) induction, lanes 6 and 11 are negative controls.

Figure 3:
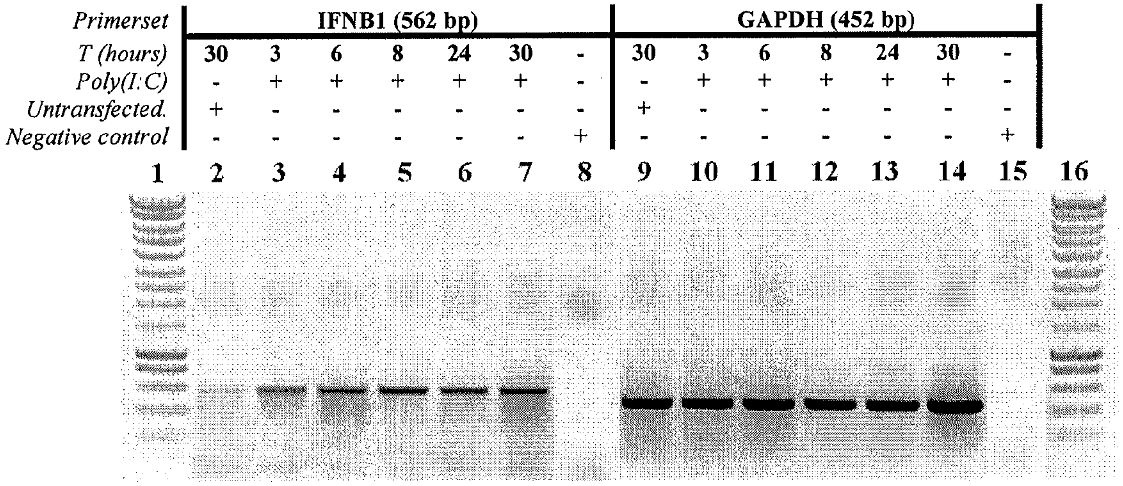

FIG. 3: Sustained IFN-β mRNA expression after transfection with poly(I:C). The + and – indicate the treatment of the cells, just as used for FIG. 2.

FIG. 4: IFN-β ELISA. FIG. 4A shows a standard curve for IFN-β ELISA, and FIG. 4B shows the actual levels of IFN-β protein measured in the medium at several moments in time.

Figure 5:
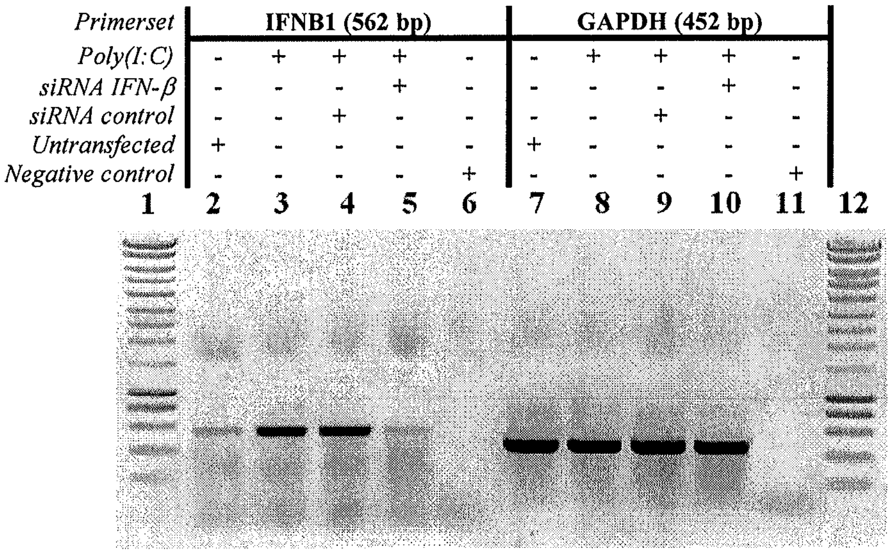

FIG. 5: Knock down of IFN-β mRNA. The + and – indicate the treatment of the cells, just as used for FIG. 2.

FIG. 6: Knock down of IFN-β protein expression. FIG. 6A shows a standard curve for IFN-β ELISA, and FIG. 6B shows the actual levels of IFN-β protein measured in the medium at several moments in time.

Figure 7:
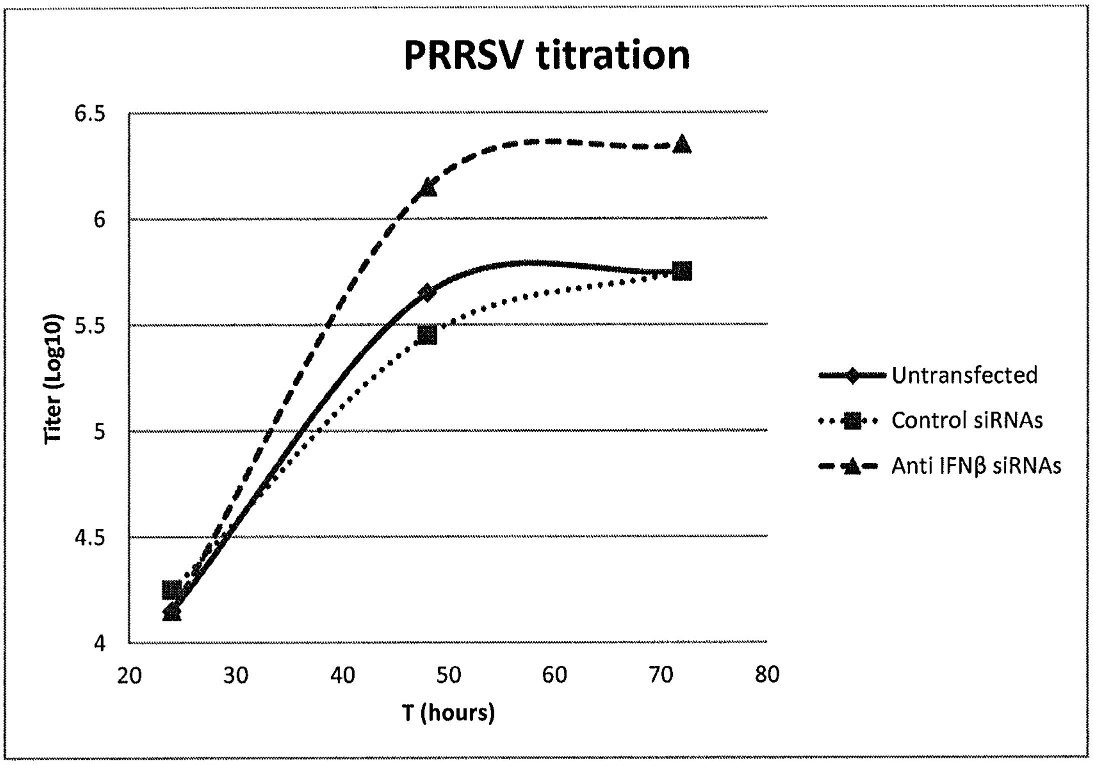

FIG. 7: PRRSV titration.

EXAMPLES

Example 1

Development of an IFN-β RT-PCR and Derivation of siRNAs

PCR primers were designed to enable the specific amplification of a section of the IFN-β mRNA of MARC-145 cells. An alignment of NM_002176.2 (*Homo sapiens* interferon beta 1 mRNA) and NM_001135795.1 (*Macaca mulatta* interferon beta 1 mRNA) was generated. Primers were designed to be complementary to conserved areas of the IFN-β mRNA sequence (FIG. 1, table 1). PCRs were performed using standard methods. As a control for the RT-PCR procedure, a PCR for GAPDH was always included in the experiments. GAPDH primer sequences are shown in table 1. The annealing temperature used for both primer sets was 55° C.

PCR samples were run on agarose gels. PCR products were excised from agarose, purified using the QIAquick Gel Extraction Kit (Qiagen) and sequenced. Custom Stealth™ siRNAs (Invitrogen) were derived by feeding the obtained MARC-145 IFN-β mRNA nucleotide sequence into the BLOCK-iT™ RNAi Designer (Life Technologies) (table 2). Negative control siRNAs (medium GC content, Life Technologies) were used in all siRNA experiments.

TABLE 1

IFN-β and GAPDH primer sequences

| Primer | Gene specificity | Expected product size (bp) | Oligonucleotide sequence (5'→3') |
|---|---|---|---|
| IFNB1 F1<br>IFNB1 R1 | Interferon beta 1 | 562 | ATGACCAACAAGTGTCTCCTC SEQ ID NO: 3<br>AGTTTCGGAGGTAACCTGTAAG SEQ ID NO: 4 |
| GAPDH FW<br>GAPDH REV | Glyceraldehyde 3-phosphate dehydrogenase | 452 | ACCACAGTCCATGCCATCAC SEQ ID NO: 5<br>TCCACCACCCTGTTGCTGTA SEQ ID NO: 6 |

TABLE 2

Anti-Marc 145 IFN-β siRNA mix.

| siRNA | Ratio | Oligonucleotide sequences (5'→3') |
|---|---|---|
| Stealth 74 | 33% | CCUGUGGCAAUUGAAUGGAAGUCUU (sense) SEQ ID NO: 7<br>AAGACUUCCAUUCAAUUGCCACAGG (anti-sense) SEQ ID NO: 8 |
| Stealth 239 | 33% | UAGCACUGGCUGGAAUGAGACUAUU (sense) SEQ ID NO: 9<br>AAUAGUCUCAUUCCAGCCAGUGCUA (anti-sense) SEQ ID NO: 10 |
| Stealth 358 | 33% | AAUUCAUGAGCAGUCUGCACCUGAA (sense) SEQ ID NO: 11<br>UUCAGGUGCAGACUGCUCAUGAAUU (anti-sense) SEQ ID NO: 12 |

Induction and Detection of IFN-β Expression in MARC-145 Cells

MARC-145 cells were propagated in medium 6/B8 modified culture medium, supplemented with 5% FCS, at 37° C. and 5% $CO_2$.

To induce an interferon response MARC-145 cells were transfected with poly(I:C). Cells were seeded on 6-wells culture plates and transfected at 90-95% confluency with 1.25-2.5 μg poly(I:C) and 5.0 μl Lipofectamine 2000 (Invitrogen), according to the manufacture's instruction.

After transfection cells were washed with PBS and lysed in 360 μl buffer RLT (RNeasy Mini Kit, Qiagen), supplemented with 1% β-mercaptoethanol. The cell lysates were collected and homogenized by 5 passages through a 21 gauge needle. RNA was isolated using the RNeasy Mini Kit (Qiagen), including the on-column DNase digestion, according to the manufacture's instruction. RNA was eluted in 50 μl $H_2O$. The eluted RNA was incubated for 10 minutes at 65° C. and at least 2 minutes on ice. The RT reaction was performed with 29 μl RNA solution, using the Ready-To-Go You-Prime First-Strand Beads (GE Healthcare) and 200 ng Random Primers (Invitrogen), in a total volume of 33 μl. Reaction mixtures were incubated 1 minute at room temperature, followed by 1 hour at 37° C. Finally, IFN-β and GAPDH PCRs were performed (as described above) and PCR samples were run on agarose gels.

In addition, cell culture medium was collected after transfection and the amount of IFN-β was determined using the VeriKine-HS Human IFN-β Serum ELISA Kit (PBL InterferonSource), according to the manufacturer's instructions.

Confirmation of siRNA Activity

The activity of the anti-IFN-β siRNAs was confirmed by co-transfections of MARC-145 cells at 30-50% confluency with 1.25 μg poly(I:C) in combination with 100 pmol anti-Marc145 IFN-β siRNA mix (or 100 pmol medium GC content negative control siRNAs), using 5.0 μl Lipofectamine 2000, followed by RT-PCRs and ELISA (as described above).

Blocking the Expression of IFN-β and PRRSV Virus Titration

One day before transfection with siRNAs, cells were seeded at a density of $1\times10^3$ cells/$cm^2$ on 6-wells culture plates. Just prior to transfection the cells were washed once with 0.01M PBS. Either 100 pmol negative control siRNAs (medium GC content, Life Technologies) or 100 pmol anti-Marc145 IFN-β siRNA mix (table 1) were transfected into the cells using 2.5 μl Lipofectamine 2000 (Invitrogen) per well, according to the manufacturer's instruction. Transfected cells were incubated for 4 to 5 hours at 37° C. and 5% $CO_2$ before being infected with PRRSV at an MOI of 0.1 in 1.0 ml culture medium per well. After 1 hour incubation at 37° C. and 5% $CO_2$ supernatant was taken off. The cells were washed once with 0.01M PBS and fresh culture medium was placed on the cells, followed by incubation at 37° C. and 5% $CO_2$ until the harvest of medium (up to 72 hours post-infection). The amount of IFN-β in medium was determined using the VeriKine-HS Human IFN-β Serum ELISA Kit (PBL Interferon-Source), according to the manufacturer's instructions.

PRRSV titration was performed by preparing ten-fold serial dilutions of medium samples in 96-wells microtiter plates containing monolayers of MARC-145 cells. After seven days of incubation at 37° C. and 5% $CO_2$ wells were screened for the presence of CPE. The virus titer was calculated according to the Spearman-Kärber method and was expressed in $\log_{10}$ $TCID_{50}$ per ml.

Results

Expression of IFN-β in MARC-145 Cells

To investigate if MARC-145 cells are able to express IFN-β, cells were transfected with poly(I:C). Cells and culture medium were harvested at several time-points post-transfection. IFN-β mRNA expression was determined by RT-PCR (FIGS. 2 and 3) and the level of expressed IFN-β protein in the medium samples was quantified using ELISA, on the basis of a standard curve (FIGS. 4*a* and *b*).

As is shown in FIG. 2, transfection of MARC-145 with poly(I:C) results in a clear induction of IFN-β mRNA expression. FIG. 3 shows that the induction of IFN-β mRNA expression is sustained for at least 30 hours.

The medium of transfected cells contains elevated levels of IFN-β protein. Similar to IFN-β mRNA, increased IFN-β protein expression can be detected for at least 30 hours (FIG. 4*b*).

Activity of Anti IFN-β siRNAs in MARC-145 Cells

The activity of the anti-IFN-β siRNAs was confirmed by transfecting MARC-145 cells with combinations of poly(I:C) and anti-Marc145 siRNA mix or medium GC content negative control siRNAs. The expression of IFN-β mRNA and protein were determined by RT-PCR and ELISA, respectively. Transfection of cells with anti-Marc145 IFN-β siRNA mix clearly results in the knock down of IFN-β mRNA (FIG. 5) and protein expression (FIG. 6). The IFN-β ELISA demonstrates that transfection of cells with both poly(I:C) and anti-Marc145 siRNA mix virtually completely abolishes the induction of IFN-β protein expression. Stimulation of IFN-β protein expression as a result of poly(I:C) transfection, but also the suppression of this effect by transfection with anti-Marc145 IFN-β siRNAs, is maintained for at least 72 hours (FIG. 6).

Enhanced PRRSV Replication after IFN-β Knock-Down in MARC-145 Cells

The effect of IFN-β knock-down on the replication of PRRSV was investigated by transfecting MARC-145 cells with anti-Marc145 IFN-β siRNA mix or medium GC content negative control siRNAs, followed by infection of these cells with PRRSV. Cell culture medium was harvested at several time-points post-transfection. The level of viral replication was determined by titration. As is shown in FIG. 7 and table 3, replication of PRRSV is most efficient in cells in which the expression of IFN-β is suppressed using siRNAs. The difference in titer increase, when the titer of virus grown on cells transfected with anti-IFN-β siRNAs is compared to negative control siRNAs, is up to 0.7 $\text{Log}_{10}$ (table 3).

TABLE3

PRRSV titration

| T (hours | Titer (Log10) Untransfected | Control siRNAs | Anti IFN-β siRNAs |
|---|---|---|---|
| 24 | 4.15 | 4.25 | 4.15 |
| 48 | 5.65 | 5.45 | 6.15 |
| 72 | 5.75 | 5.75 | 6.35 |
| Titer increase | 1.6 | 1.5 | 2.2 |

The invention claimed is:

1. A mammalian cell that is deficient in its IFN-β production due to a deliberate blocking of IFN-β production in the cell;

wherein when the cell is infected with a porcine reproductive and respiratory syndrome virus (PRRSV) said deliberate blocking is additional to the blocking effect of the PRRSV; and wherein the cell is capable of propagating the PRRSV.

2. The mammalian cell of claim 1, wherein said cell comprises a DNA fragment encoding an siRNA under the control of a suitable promoter, that is capable of silencing a gene of the IFN-β pathway.

3. The mammalian cell of claim 2, which is selected from the group of mammalian cells consisting of a MA104 cell and a Marc145 cell.

4. The mammalian cell of claim 3, wherein said mammalian cell is infected with PRRSV.

5. A cell culture comprising the mammalian cell of claim 4.

6. A method for propagating PRRSV comprising the step of propagating PRRSV on the cell culture of claim 5.

7. The mammalian cell of claim 1, wherein said cell has a mutation in a gene of the IFN-β pathway.

8. The mammalian cell of claim 7, which is selected from the group of mammalian cells consisting of a MA104 cell and a Marc145 cell.

9. The mammalian cell of claim 8, wherein said mammalian cell is infected with PRRSV.

10. A cell culture comprising the mammalian cell of claim 9.

11. A method for propagating PRRSV comprising the step of propagating PRRSV on the cell culture of claim 10.

12. The mammalian cell of claim 7, wherein said gene is selected from the group of genes consisting of the genes encoding IFN-β, the IFN-α/β receptor, MyD88, IRAK-4, IRAK-1, TRAF3, the genes encoding the IKK-α subunit and IRF7.

13. The mammalian cell of claim 1, which is selected from the group of mammalian cells consisting of a MA104 cell and a Marc145 cell; wherein the MA104 cell and the Marc145 cell are deficient in its IFN-β production due to a deliberate blocking of IFN-β production in that cell.

14. The mammalian cell of claim 1, wherein said mammalian cell is infected with PRRSV.

15. A cell culture comprising the mammalian cell of claim 14.

16. A method for propagating PRRSV comprising the step of propagating PRRSV on the cell culture of claim 15.

17. A cell culture comprising the mammalian cell of claim 1.

* * * * *